(12) United States Patent
Pflanz

(10) Patent No.: US 10,184,101 B2
(45) Date of Patent: Jan. 22, 2019

(54) NUTRIENT MEDIUM UNIT AND METHOD FOR HOLDING A FILTER FROM A FILTRATION DEVICE

(75) Inventor: Karl Pflanz, Gleichen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 0 days.

(21) Appl. No.: 12/450,198

(22) PCT Filed: Feb. 16, 2008

(86) PCT No.: PCT/EP2008/001213
§ 371 (c)(1),
(2), (4) Date: Sep. 14, 2009

(87) PCT Pub. No.: WO2008/113444
PCT Pub. Date: Sep. 25, 2008

(65) Prior Publication Data
US 2010/0028933 A1    Feb. 4, 2010

(30) Foreign Application Priority Data

Mar. 21, 2007  (DE) .................. 10 2007 014 081
Jan. 24, 2008  (DE) .................. 10 2008 005 968

(51) Int. Cl.
*B01L 9/00*   (2006.01)
*C12M 3/00*   (2006.01)
(Continued)

(52) U.S. Cl.
CPC ............ *C12M 23/10* (2013.01); *C12M 23/00* (2013.01); *C12M 23/38* (2013.01); *C12M 23/46* (2013.01);
(Continued)

(58) Field of Classification Search
CPC ...... C12M 23/10; C12M 23/38; C12M 23/46; C12M 33/14; C12M 23/00; C12M 29/04;
(Continued)

(56) References Cited

U.S. PATENT DOCUMENTS 4,280,002 A * 7/1981 Bailey et al. .............. 435/305.4
4,299,921 A * 11/1981 Youssef ..................... 435/305.4
(Continued)

FOREIGN PATENT DOCUMENTS

DE    2157150     11/1971
DE    19823993    12/1999
(Continued)

*Primary Examiner* — Jennifer Wecker
(74) *Attorney, Agent, or Firm* — Gerald E. Hespos; Michael J. Porco; Matthew T. Hespos

(57) ABSTRACT

The invention relates to a nutrient medium unit for holding a filter of a filtration device, comprising a lower part that is filled with the nutrient medium and a lid, the latter having a fixing edge that protrudes into the lower part and that can be connected to an edge of the filter by means of an adhesive bond in order to remove said filter from the filtration device. The invention also relates to a method for the microbiological analysis of liquid samples, according to which a membrane filter is lifted off a filter support and laid on the surface of a nutrient medium that is situated in a lower part of a nutrient medium unit. The lower part is then covered by a lid, the latter being placed on the membrane filter lying on the filter support in such a way that a fixing edge located in the lid is connected to an edge of the filter by means of an adhesive bond. The lid and the attached filter are lifted off the filter support and placed on the dish-shaped lower part of the nutrient medium unit.

23 Claims, 5 Drawing Sheets

(51) Int. Cl.
  *C12M 3/06* (2006.01)
  *C12M 1/00* (2006.01)
  *C12M 1/22* (2006.01)
  *C12M 1/26* (2006.01)
  *B01L 3/02* (2006.01)
  *C12Q 1/02* (2006.01)
  *G01N 1/40* (2006.01)
  *B01L 3/00* (2006.01)

(52) U.S. Cl.
  CPC ............ *C12M 29/04* (2013.01); *C12M 33/14* (2013.01); *B01L 3/502* (2013.01); *B01L 3/5635* (2013.01); *B01L 2200/141* (2013.01); *B01L 2300/042* (2013.01); *B01L 2300/048* (2013.01); *B01L 2300/0681* (2013.01); *B01L 2300/161* (2013.01); *G01N 2001/4088* (2013.01)

(58) Field of Classification Search
  CPC ......... B01L 2200/141; B01L 2300/042; B01L 2300/048; B01L 2300/0681; B01L 2300/161; B01L 3/502; B01L 3/5635; G01N 2001/4008
  USPC ................ 422/513, 560, 561; 435/288.3
  See application file for complete search history.

(56) References Cited

U.S. PATENT DOCUMENTS

| | | | |
|---|---|---|---|
| 4,668,633 A | | 5/1987 | Walton |
| 4,777,137 A | | 10/1988 | Lemonnier |
| 5,139,951 A | | 8/1992 | Butz et al. |
| 5,272,083 A | * | 12/1993 | Butz et al. .................... 435/401 |
| 5,958,762 A | | 9/1999 | Stoppini et al. |
| 2002/0096468 A1 | | 7/2002 | Zuk, Jr. |
| 2004/0063169 A1 | * | 4/2004 | Kane ............................... 435/30 |
| 2004/0209349 A1 | | 10/2004 | Goldman et al. |
| 2006/0076081 A1 | * | 4/2006 | Gleichauf et al. ............. 141/326 |
| 2006/0172412 A1 | * | 8/2006 | Perrier et al. .............. 435/297.5 |
| 2007/0084862 A1 | * | 4/2007 | Jakab et al. .................. 220/4.01 |
| 2007/0175897 A1 | | 8/2007 | Ellson |
| 2007/0212750 A1 | * | 9/2007 | Kieffer et al. ................. 435/34 |
| 2010/0233800 A1 | * | 9/2010 | Carlo ........................ 435/305.4 |

FOREIGN PATENT DOCUMENTS

| | | | | |
|---|---|---|---|---|
| DE | 10 2005 008 220 B3 | | 8/2006 | |
| EP | 0150775 | | 11/1988 | |
| EP | 463897 A1 | * | 1/1992 | ........... B01D 29/085 |
| GB | 2083376 A | * | 3/1982 | ............. G09F 3/02 |
| WO | WO 9700314 A1 | * | 1/1997 | ............. C12M 3/06 |
| WO | WO 00/17315 A | | 3/2000 | |

\* cited by examiner

NUTRIENT MEDIUM UNIT AND METHOD FOR HOLDING A FILTER FROM A FILTRATION DEVICE

The invention relates to a nutrient medium unit for holding a filter of a filtration device having a lower part, filled with nutrient medium, and a lid.

Furthermore, the invention relates to a method for the microbiological analysis of liquid samples after prior filtration in the case of which a membrane filter is lifted from a filter support and laid down on a surface of a nutrient medium arranged in a lower part of a nutrient medium unit, and the lower part is covered by a lid.

In order to conduct the microbiological analysis of liquids or samples to be filtered with the aid of a membrane filter, after the filtration the filter is removed and, for example, laid in a Petri dish with a nutrient medium of agar and covered with a lid, wherein the nutrient medium unit is stored in an incubator for a number of days at an elevated temperature. Via the nutrient medium, the possibly present microorganisms obtain nutrients which stimulate growth such that said microorganisms can be determined or counted.

PRIOR ART

Thus, for example, DE 10 2005 008 220 B3 discloses a filtration device having a membrane filter arranged on a filter support of a lower part of the device, and having an attachment that can be placed on the lower part of the device.

This device, which has proved itself in principle, has the disadvantage of requiring a special removal ring which can be expanded and used to remove the membrane filter and to lay down the membrane filter in a dish-shaped lower part of the nutrient medium unit.

Furthermore, DE 198 23 993 B4 discloses a disposable device for determining germ numbers in liquids with the aid of a pouring funnel, a microporous membrane with membrane carrier and a membrane support unit, it being possible to fix the pouring funnel and the membrane carrier to one another, and at least one ejection device for the membrane carrier being provided at the pouring funnel and the membrane carrier and the ejection device being releaseably gripped by a membrane support unit.

It is disadvantageous in this case that the filtration unit is of relatively complicated design, and that the filter support must be released after the filtration in a separate step via a defined pressure point. Thereafter, it is necessary in a second additional step for the pouring funnel/membrane carrier unit to be positioned over the open lower part of the nutrient medium unit, that is to say the agar dish, and for the membrane to be laid down on the nutrient medium by means of a second pressure point offset by 90°.

Furthermore, EP 0 150 775 B1 discloses a device for analyzing a liquid sample by means of membrane filtration, in the case of which the membrane filter is fastened sealingly at the end of a sleeve. This sleeve end is designed such that it serves as a plug-in receptacle for a medium container. The second sleeve end can be tightly closed with a lid in order to put the membrane medium unit into the incubator in a closed state.

A disadvantage here is a fixed connection to the pouring funnel that requires either that a large dead volume be accepted, or else that there be a need for additional handling steps to reduce the dead volume by compression, or else to separate the unit.

Furthermore, US 2002/0096468 A1 discloses a nutrient medium unit that is assembled from parts of a filtration device. After a filtration operation, a lid and an attachment or funnel is removed from a lower part of the device, on which a filter is arranged on a filter support designed as a pad. In this case, the filter is permanently bonded to the lower part of the device with a fixing edge that acts as a seal. The lid of the attachment is placed directly on the lower part of the filtration device and the lower part of the device and lid are turned over with the filter such that the lid forms a lower part. Subsequently, nutrient solution is fed via the outflow of the lower part of the device, and the outflow is closed with a special stopper. Only then is it possible to insert the device into an incubator.

The known device has the disadvantage that the filtration device is relatively cost intensive owing to the multiplicity of its parts, and that the lower part of the device is not available for further filtration, at least during an incubation time in the incubator. If the filter is bonded in the lower part of the device, the filter support cannot be exchanged, but is merely relatively laboriously soaked with a nutrient solution. Thus, in this known device either the filter remains in the lower part of the filtration device, or the filter is removed in a known way with a tool, for example, forceps.

U.S. Pat. No. 4,299,921 A discloses a nutrient medium unit that has a seal between its lower part and its lid. The seal is either fastened on the edge of the lower part or in the lid by way of an adhesive layer.

This known nutrient medium unit has the disadvantage that it is necessary to insert a filter from a filtration device with, for example, forceps.

OBJECT

An object of the present invention is therefore to provide a device and a method in the case of which it is possible to insert the filter into the nutrient medium unit simply and cost effectively after the filtration without a complicated filtration device and without the use of an additional aid.

The object relating to the device or nutrient medium unit is achieved in conjunction with the preamble of claim 1 by virtue of the fact that the lid has a fixing edge which protrudes into the lower part and can be connected to the filter by an edge of the filter via an adhesive bond in order to remove the filter from the filtration device.

Because the lid has a fixing edge that can be placed on a corresponding edge of the filter via an adhesive bond, the filter bonds to the lid and can easily and simply be lifted from the filter support and inserted into the lower part of the nutrient medium unit. In this case, it is possible on the one hand to use conventional uncomplicated filtration devices, while on the other hand the filter can be inserted into the nutrient medium unit without an additional tool.

According to a preferred embodiment of the invention, the adhesive bond is of temporary or reversible design. Consequently, the lid can be easily removed or lifted from the filter after incubation.

According to a preferred embodiment of the invention, the adhesive bond is designed as an adhesive layer made from a suitable adhesive and can be arranged on the fixing edge of the lid or on the corresponding edge of the filter. The strength of the adhesive bond can be selected such that it is possible subsequently to analyze the sample after incubation by withdrawing the filter again from the nutrient medium or the fixing edge of the lid, and thus gaining access to the microbiological colonies formed.

According to a further preferred embodiment of the invention, the adhesive layer is formed from a PSA-dispersion adhesive or from acrylate copolymer microspheres.

Even wet filters can thereby be adequately bonded on the fixing edge of the lid, and also be withdrawn again. Suitable pressure sensitive adhesives are known to the person skilled in the art for example as acrylate adhesives based on microspheres.

In accordance with a further preferred embodiment, the adhesive layer is designed in such a way that it has as high an adhesive strength as possible for the removal of the filter from the filtration device and can be released again with a time delay after the contact with the moist filter and the moist nutrient medium, and the adhesive strength drops to zero. The required time delay results from the application. The adhesive strength must be available for a number of minutes in order to manipulate the filter after which it is to drop to zero. It should be possible to release the fixing edge of the lid from the filter once more, at least at the final instant of incubation. In the case of classical microbiology, the final instant of the incubation comes about when colonies visible to the eye occur after approximately one day. The incubation period is usually defined in norms and can last up to a number of days. In the case of quick tests, which can already detect germs and microcolonies in advance, the adhesive strength should already have dropped after approximately 1 h at the latest to such an extent that the filter can be released from the fixing edge of the lid without being destroyed.

In accordance with a preferred embodiment of the invention, this time offset adhesion/release behavior is brought about by an inter layer of a water soluble compound under the adhesive layer. This soluble layer is applied between the surface of the fixing edge and the adhesive layer in such a way that the entire adhesive surface is reliably underlaid by the soluble layer, and that contact surfaces are also still present for the intrusion of the water required for the dissolution. Such a function is fulfilled by gelatin, for example. The water required for the dissolution will diffuse from the agar after being placed on the agar surface. All chemicals used in the soluble layer, as also in the adhesive, are not permitted to exert a negative influence on the intended growth of the microorganisms.

It is also possible for the water soluble intermediate layer to be arranged on the edge of the lid, and for the adhesive layer to be arranged on the edge of the filter.

In accordance with a further preferred embodiment of the invention, the fixing edge is formed by a free end face of an annular inner wall that is arranged on the lid inner surface facing the lower part and protrudes into the lower part. The annular inner wall firstly ensures the required spacing between the filter and lid, and secondly its diameter in the dimension of the filter diameter is configured such that the filter comes into contact with the adhesive layer of the adhesive bond only on its outwardly lying edge, the edge being arranged outside the filter surface used.

In accordance with a further preferred embodiment, the annular inner wall is designed such that the fixing surface is not planar, but is concavely cambered towards two predetermined sides such that when the filter is removed from the filter support during use one of these two sides is firstly released, and thus the residual vacuum remaining after the vacuum filtration is further broken and the filter can thereby be removed more easily. Even when the filter is placed on the agar surface, a positive effect thereby results, since the inclusion of air bubbles is further reduced.

The lower part of the nutrient medium unit is of dish-shaped design and has a nutrient medium on whose top side facing the lid the filter adhering to the lid can be laid down. After the placement of the lid on the lower part, the filter and the top side of the nutrient medium lie against one another evenly and without any spacing. The lower part can be, for example, a Petri dish that is filled with nutrient medium. Consideration is given as nutrient media to agar based media and also to cardboard discs filled with aqueous nutrient media.

In accordance with a further preferred embodiment of the invention, the top side of the nutrient medium is convexly cambered.

Because the nutrient medium or the agar is convexly cambered, that is to say is higher in the middle, the filter or the membrane firstly makes contact in the middle upon placement, and so, upon its being further laid down, the air can escape outwards and no air bubbles can form. This is desirable, since air bubbles could otherwise be enclosed between the filter and nutrient medium, something which could lead to an inhibition of growth.

After placement of the lid on the lower part, the filter and the top side of the nutrient medium lie against one another evenly and without any spacing.

According to a further preferred embodiment of the invention, a support ring which supports the nutrient medium laterally in a lower region and whose inside diameter corresponds approximately to the outside diameter of the filter is arranged concentrically with the outer wall of the lower part.

Less agar is used by the support ring, since only the filter surface is underlaid with agar. The reinforcement ring further has the advantage that the surface of the nutrient medium or of the agar plate can be more easily cambered. This embodiment also ensures that the adhesive properties can be varied by the agar owing to the avoidance of contact between the adhesive and the agar.

In accordance with a further preferred embodiment of the invention, the support ring is positioned and designed such that by making contact or closure with the adhesive layer of the lid it reduces any possible variation, for example by drying out, in the adhesive properties during storage.

According to a further preferred embodiment of the invention, the inside diameter of the outer wall of the lid is selected such that it is greater than the outside diameter of the filter support of the filtration device. The inside diameter of the outer wall of the lid is preferably only slightly greater than the outside diameter of the filter support. Consequently, when being placed on the filter, the lid is guided by the filter support before the filter or the lid comes into contact with the adhesive bond. The correct positioning of the filter in the lid is thereby ensured.

In a further preferred embodiment, the annular inner wall of the lid has an inside radius that is greater than or equal to the sealing inner edge of the filtration funnel. It is thereby ensured during the positioning that no filtration surface is covered, and thereby potentially filtered germs are prevented from growing. Since commercial filters (prescribed by the international references and proposals regarding standards) have a total diameter of 47 mm, the commercial filtration funnels are available in similar diameters, and so this inventive embodiment can to a large extent also be offered for all current filtration funnels.

In accordance with a further preferred embodiment of the invention, the adhesive bond between the fixing edge and filter is interrupted in places. In a preferred embodiment, the fixing edge or the annular inner wall have at least one cutout through which an exchange of air can take place. However, it is also possible for example to use two cutouts to subdivide the annular inner wall into at least two inner wall segments with end faces in the shape of circular arc segments of variable length. These end faces in the shape of circular arc segments that form the fixing edge in this embodiment can be fixed on the outer edge of the filter via the adhesive layer of the adhesive bond, the edge being arranged outside the filter surface used. The adhesive bond can be arranged on the end faces in the shape of circular arc segments, or on the corresponding edge of the filter.

In a further preferred embodiment, the at least two cutouts are configured to be so wide that the fixing edge or the annular inner wall is reduced to at least two fixing pins that form the fixing edge and whose free ends, averted from the inner surface of the lid, can be fixed on the outer edge of the filter via the adhesive layer of the adhesive bond, the edge being arranged outside the filter surface used. In a particularly preferred embodiment, the adhesive layer is applied only to the free ends of the fixing pins. These two preferred embodiments do not only render it possible to economize on the material used for the annular inner wall, but also ensure an exchange of air.

However, it is also possible, in order to ensure an exchange of air, to design the lid with a recloseable gas-feed aperture for feeding gas to the filter surface, in order to ensure an adequate exchange of air for aerobic germs, and thus to ensure the supply of oxygen during the incubation.

The filters are preferably designed as membrane filters.

The further object with reference to the method is achieved in conjunction with the preamble of claim 23 by virtue of the fact that the lid is placed on the filter lying on the filter support such that a fixing edge arranged in the lid is connected to an edge of the filter via an adhesive bond and in that the lid with the adhering filter is lifted from the filter support and placed on the dish-shaped lower part of the nutrient medium unit such that the underside, averted from the lid, of the filter rests on the top side facing the lid, of the nutrient medium.

Owing to the fact that the filter is bonded to the lid and the lid is lifted with the filter from the filter support and placed on the top side of the nutrient medium arranged in the nutrient medium container, additional steps or devices are avoided, and the filter can be moved without an additional tool into the dish-shaped lower part of the nutrient medium unit. It is possible to use simple, conventional filtration devices. As long as an adhesive bond is arranged on the lid, there is not even a need to modify the filter.

The result is a simple and cost effective manipulation of the filter with the applied sample.

In accordance with a preferred embodiment of the invention, a water-soluble intermediate layer applied to the fixing edge of the lid is dissolved, and the lid can be released from the filter again after an incubation.

Further features of the invention emerge from the following detailed description and the attached drawings in which preferred embodiments of the invention are illustrated by way of example.

DESCRIPTION OF THE EXEMPLARY EMBODIMENTS

Figure 1:
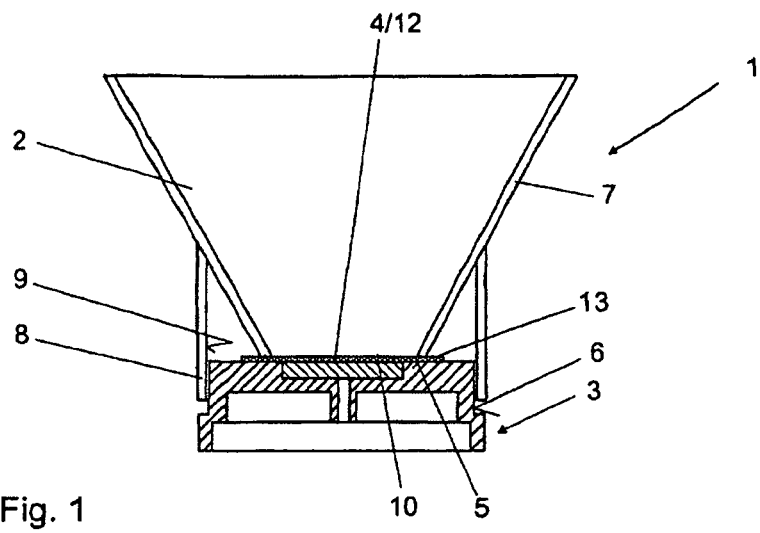
FIG. 1 shows a side view of a filtration device in section.

A filtration device 1 essentially comprises an attachment 2, a lower part 3 of the device, and a filter 4.

The lower part 3 of the device has a filter support 5 on which the filter 4 is laid down. The lower part 3 of the device further has a base 6 for holding the attachment 2.

The attachment 2 is designed as a funnel 7 that has on its lower end (in a vertical direction) a cylindrical neck 8 that engages with its inner lateral surface 9 over the base 6 of the lower part 3. In the inner region of the cylindrical neck 8, the funnel 7 has an outlet opening 10 that serves as a stop against the lower part 3 of the device or against the filter 4 arranged on the lower part 3. The attachment 2 or the funnel 7 can be latched against the lower part 3 via a latch 11.

The filter 4 comprises a membrane 12 with a filter edge 13 that is arranged outside the outlet opening 10.

Figure 4:
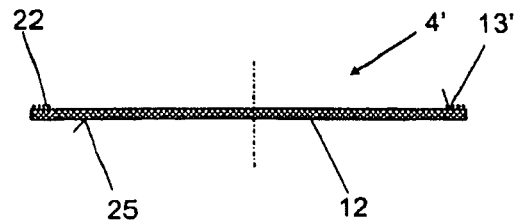
FIG. 4 shows a side view of a filter with an adhesive layer, in section and in an enlarged illustration.

According to the embodiment of FIG. 4, the filter edge 13' of the filter 4' is provided with an adhesive bond 22.

After the filtration of the sample, the filter 4, 4' is inserted into a nutrient medium unit 14. The nutrient medium unit 14 comprises a dish-shaped lower part 15 that can be designed as a Petri dish or an agar plate, and a lid 16. A nutrient medium 17, for example made from agar, is arranged in the lower part 15.

Figure 5:
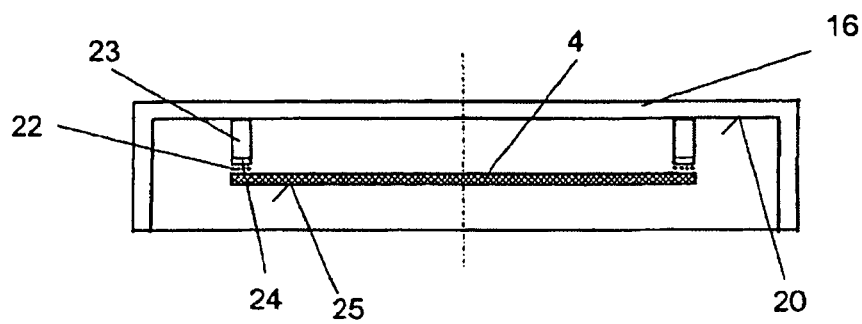
FIG. 5 shows a side view of the lid from FIG. 3 with the bonded filter, in section and in an enlarged illustration.
Figure 6:
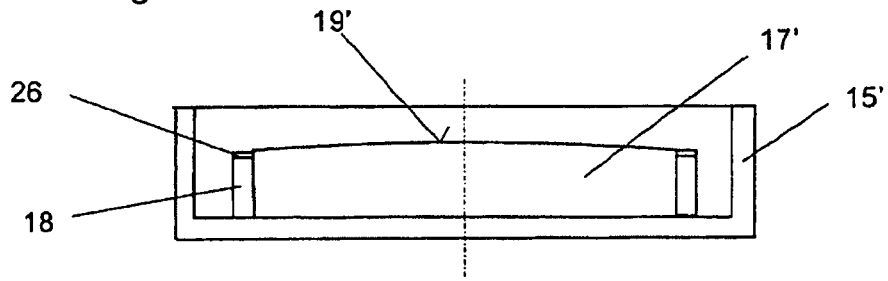
FIG. 6 shows a side view of a lower part of a nutrient medium unit with convexly cambered nutrient medium and support ring, in section and in an enlarged illustration.

In accordance with the exemplary embodiment of FIGS. 5 and 6, the lower part 15' has a support ring 18 that laterally supports the nutrient medium 17'. In the unloaded state, the top side 19, 19' of the nutrient medium 17, 17', which is at the top in the vertical direction, is convexly cambered such that the nutrient medium 17, 17' is somewhat thicker towards the middle.

Figure 2:
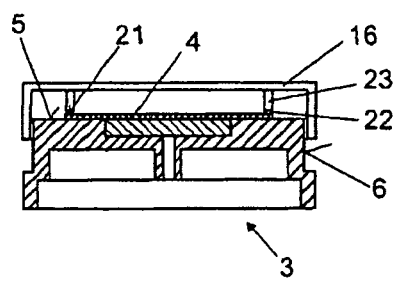
FIG. 2 shows a side view of the lower part of the device from FIG. 1 with filter and a lid of a nutrient medium unit placed on, in section.
Figure 3:
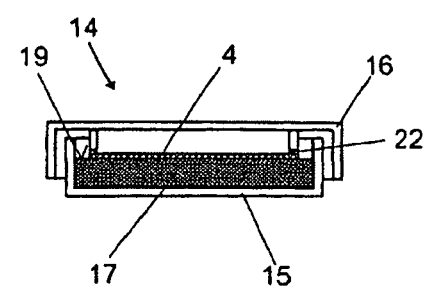
FIG. 3 shows a side view in section of the lower part of a nutrient medium unit with a lid placed on and a filter inserted.

The lid 16 of FIG. 2 or 5 can be placed on the lower part 15, 15' of FIG. 3 or 6 of the nutrient medium unit 14. On its inner surface 20 facing the lower part 15, 15', the lid 16 has a fixing edge 21 that protrudes into the lower part 15, 15' and, for the purpose of removing the filter 4, 4' from the filtration device 1, can be connected to the filter 4, 4' via the adhesive bond 22 by means of the filter edge 13 of the filter 4, 4'. The fixing edge 21 is formed by a free end face of an annular inner wall 23 arranged on the inner surface 20 of the lid.

Figure 7:
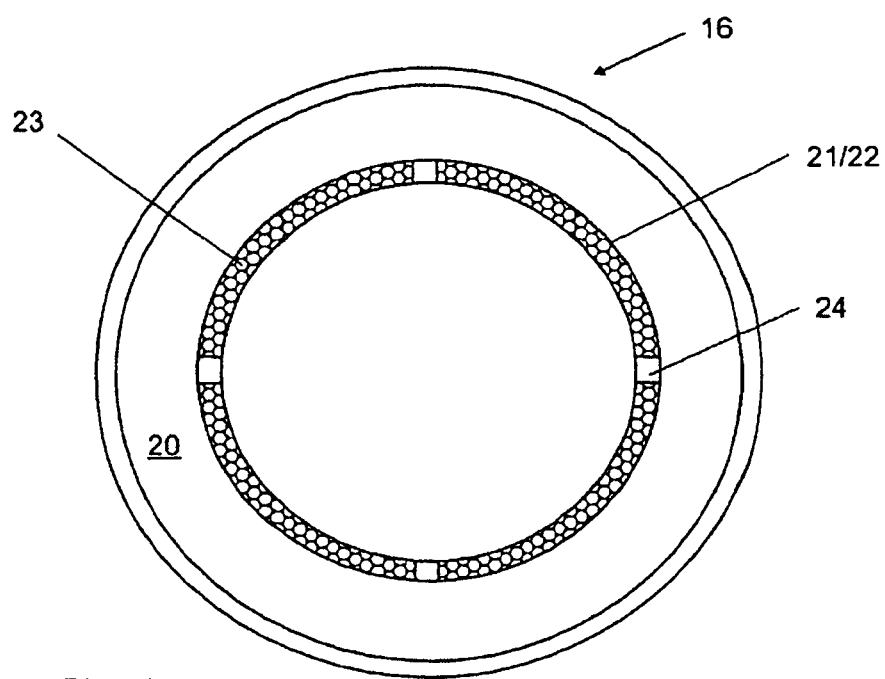
FIG. 7 shows a bottom view of the lid from FIG. 5 with an adhesive layer, in an enlarged illustration.
Figure 8:
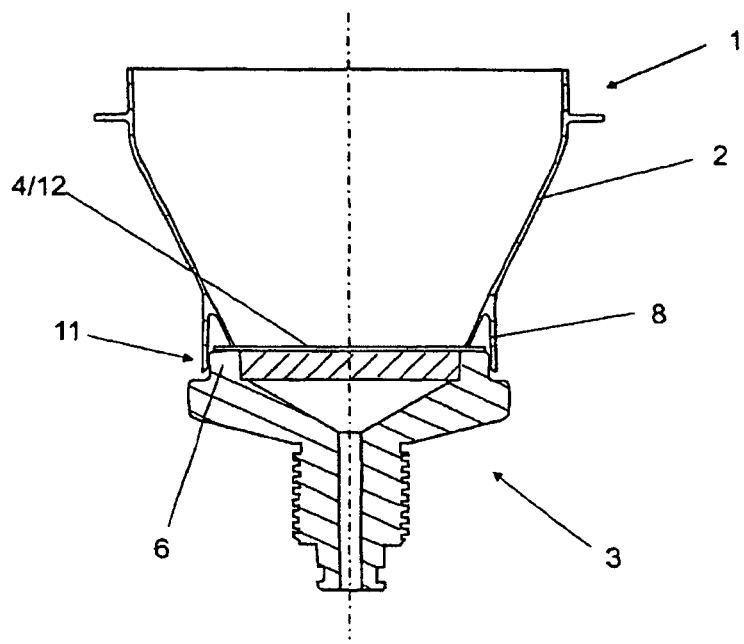
FIG. 8 shows a side view of a further filtration device in section.
Figure 9:
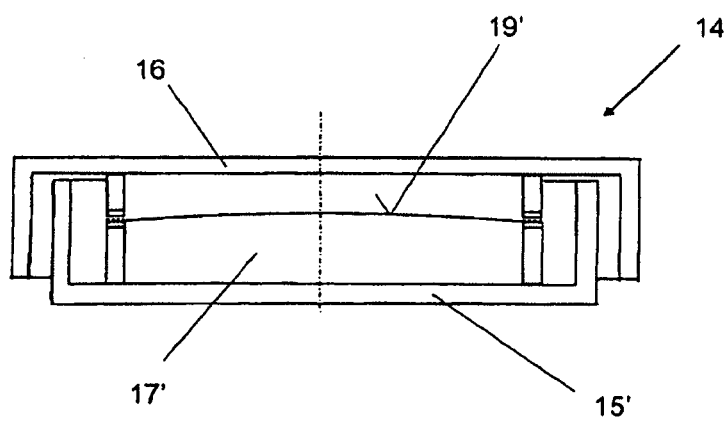
FIG. 9 shows a side view of a nutrient medium unit without a filter, in section.

In accordance with FIG. 7, the adhesive bond 22 is arranged as an adhesive layer, made from a suitable adhesive, on the fixing edge 21 of the lid 16. However, it is also possible in accordance with FIG. 4 to arrange the adhesive layer on the filter edge 13'.

The adhesive bond 22 between the fixing edge 21 and filter 4 is interrupted in places in order to ensure an exchange of air. For this purpose, the inner wall 23 of the lid 16 has cutouts 24 on its end face or on the fixing edge 21. It is also possible to arrange cutouts 26 on the support ring 18. The adhesive layer of the adhesive bond 22 is formed from an adhesive comprising PSA dispersion adhesive or acrylate copolymer microspheres.

Figure 10:
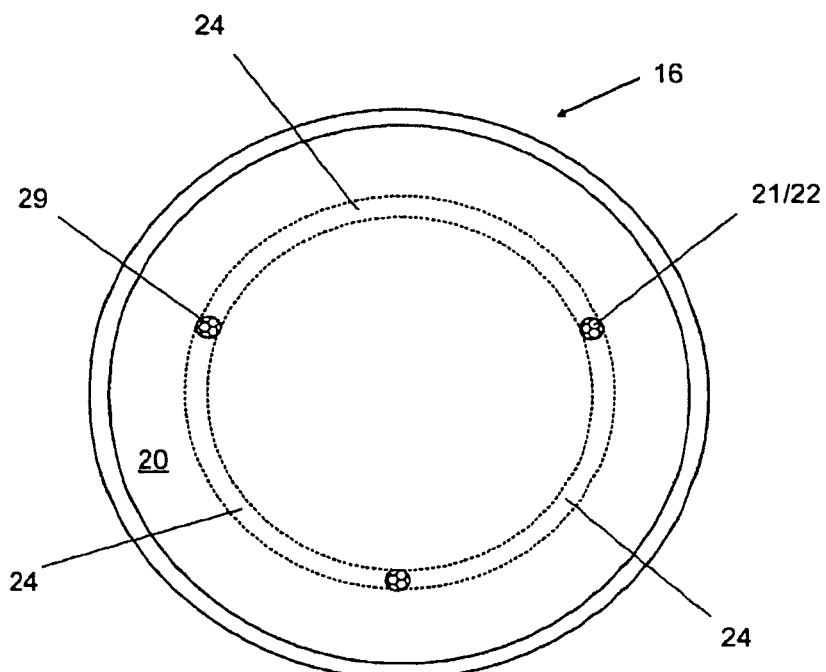
FIG. 10 shows a bottom view of the lid corresponding to FIG. 5, in an enlarged illustration with fixing pins.

In a preferred embodiment in accordance with FIG. 10, the cutouts 24 are configured to be so wide that the annular inner wall 23 or the fixing edge 21 in FIG. 2 is reduced in FIG. 10 to at least two fixing pins 29 whose free ends, averted from the inner surface 20 of the lid, can be fixed on the outer edge 13' of the filter 4' of FIG. 4 via the adhesive layer of the adhesive bond 22, the outer edge 13' being arranged outside the filter surface used. In this case, the adhesive layer or adhesive bond 22 is applied to the free ends. In the case of an alternative embodiment not illustrated here, the fixing pins 29 have no adhesive layer at their free ends. The adhesive layer is arranged in this case on the filter edge 13. At least two fixing pins 29 are provided for the bond between the filter 4 or 4' and lid 16, for reasons of stability. FIG. 10 shows three fixing pins 29, the latter preferably being arranged equidistantly on an imaginary circular circumference.

Figure 11:
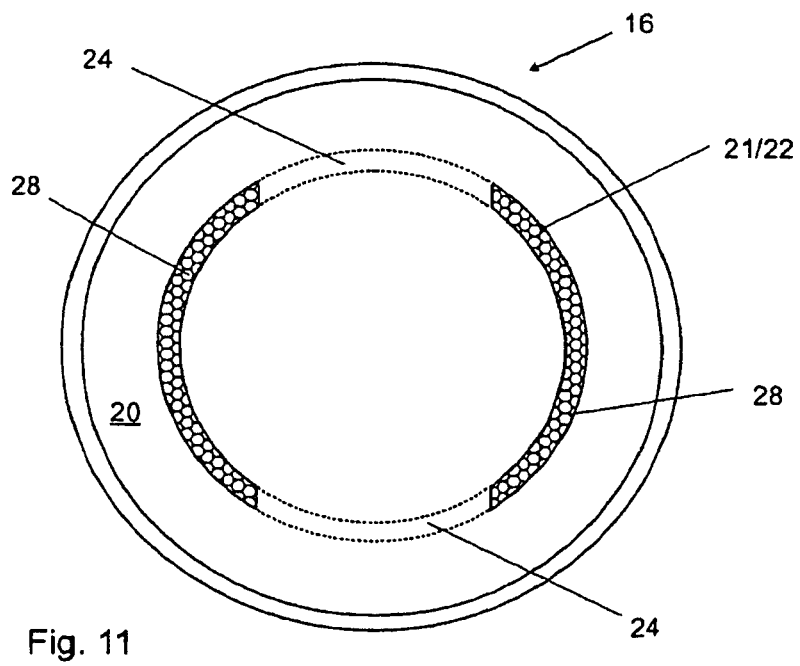
FIG. 11 shows a bottom view of a lid corresponding to FIG. 5, in an enlarged illustration with inner wall segments.

The exemplary embodiment of FIG. 11 shows an alternative embodiment of a lid 16, whose fixing edge 21 is formed by two inner wall segments 28 with cutouts 24 lying there between.

In order to insert the filter 4 designed as a membrane filter into the lower part 15, 15' of the nutrient medium unit 14, the attachment 2 is lifted from the filter support 5 of the lower part 3 of the device after the filtering. Subsequently, the lid 16 is removed from the lower part 15, 15' of the nutrient medium unit 14, and placed on the filter 4 lying on the filter support 5 such that the fixing edge 21 arranged in the lid 16 is connected to the filter edge 13 of the filter 4 via the adhesive bond 22, and the filter 4 is bonded on the lid 16. The lid 16 is then lifted with the filter 4 from the filter support 5 and placed on the lower part 15, 15' of the nutrient medium unit 14. In this case, the lid 16 is placed with the underside of the filter 4 on the top side 19, 19' of the nutrient medium 17, 17'.

Figure 12:
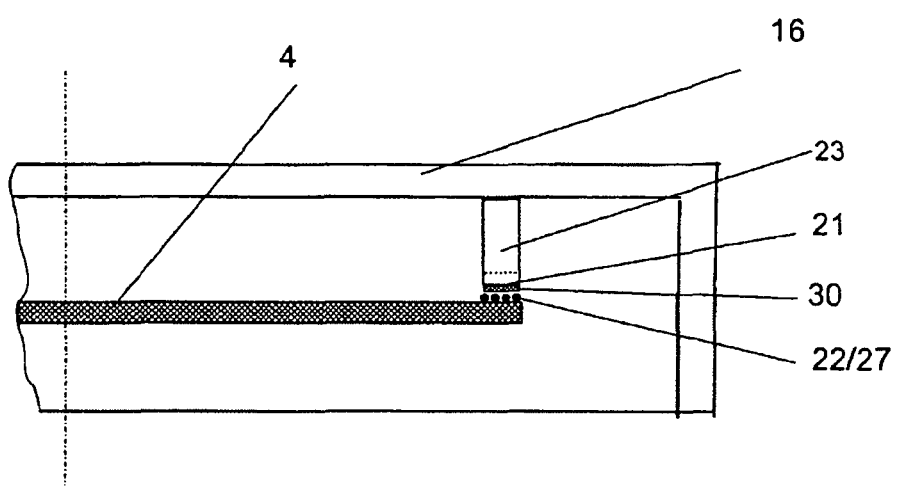
FIG. 12 shows a side view of a lid with a water-soluble intermediate layer, adhesion layer and bonded filter, in section and outline and in an enlarged illustration.

According to the exemplary embodiment of FIG. 12, a water-soluble intermediate layer 30 made from gelatin is applied between the adhesive layer 27 of the adhesive bond 22 and the fixing edge 21 of the lid 16.

The invention claimed is:

1. A nutrient medium unit (14) for holding a filter (4, 4') from a filtration device (1), the filter (4, 4') having opposite first and second surfaces and an outer peripheral edge (13) extending between the first and second surfaces, the nutrient medium unit comprising:
a lower part (15, 15') with a support ring and being filled with nutrient medium inward of the support ring;
a lid (16) having a top wall, an outer wall projecting from the top wall and telescoped over the lower part (15, 15') outward of the support ring, an annular inner wall (23) projecting from the top wall at positions inward of the outer wall, an end of the annular inner wall from the top wall and facing away from the top wall defining a fixing edge that is dimensioned to register with the first surface of the filter (4, 4') in proximity to the outer peripheral edge of the filter; and
an adhesive (22, 27) applied to the end of the fixing edge (21) of the annular inner wall (23) and bonding the annular inner wall (23) to the filter (4, 4') in order to remove the filter from the filtration device, the annular inner wall (23) of the lid (16) projecting from the top wall thereof a sufficient distance so that areas of the second surface of the filter (4, 4') inward of the annular inner wall (23) contact the nutrient medium when the lid (16) is telescoped over the lower part (15, 15').

2. The nutrient medium unit of claim 1, wherein the adhesive (22) is a temporary or reversible adhesive.

3. The nutrient medium unit of claim 1, wherein the adhesive (27) is applied to the fixing edge (21) of the lid (16).

4. The nutrient medium unit of claim 3, wherein the adhesive is applied to the fixing edge of the lid via a water-soluble intermediate layer (30).

5. The nutrient medium unit of claim 1, wherein the adhesive (22, 27) is applied to the first surface of the filter (4, 4') adjacent the outer peripheral edge (13) of the filter (4').

6. The nutrient medium unit of claim 5, wherein the fixing edge (21) of the lid (16) has a water-soluble layer (30).

7. The nutrient medium unit of claim 3, wherein the adhesive (27) is a PSA-dispersion adhesive or acrylate copolymer microspheres.

8. The nutrient medium unit of claim 1, wherein the fixing edge (21) defines a fixing surface that is concavely cambered towards two predetermined sides.

9. The nutrient medium unit of claim 1 wherein the lower part (15, 15') is dish-shaped and has a nutrient medium (17, 17') on whose top side (19, 19') facing the lid (16) the filter (4, 4') adhering to the lid (16) can be laid down.

10. The nutrient medium unit of claim 9, wherein the top side (19, 19') of the nutrient medium (17, 17') is convexly cambered.

11. The nutrient medium unit of claim 9, wherein the lower part (15') has an outer wall, the support ring (18) that supports the nutrient medium (17') laterally in the lower part (15') has an inside diameter that corresponds approximately to the outside diameter of the filter (4, 4') and is arranged concentrically within the outer wall of the lower part (15').

12. The nutrient medium unit of claim 11, wherein the support ring (18) is positioned and designed such that by making contact or closure with the adhesive layer (27) of the lid (16) the support ring (18) reduces any possible variation in the adhesive properties during storage.

13. A nutrient unit medium comprising:
a filtration device (1) having a filter support (5);
a filter supported removably on the filter support (5), the filter having an outer peripheral edge (13, 13') and being continuous at all positions inward of the outer peripheral edge (13, 13');
a lower part (15, 15') with a support ring and being filled with nutrient medium inward of the support ring; and
a lid (16) having a top wall, an outer wall projecting from the top wall and having an inside diameter that is greater than the outside diameter of the filter support of the filtration device (1) and greater than an outside diameter of the lower part (15, 15'), the lid (16) further having an annular inner wall (23) projecting from the top wall at locations inward of the outer wall, and end of the annular inner wall (23) remote from the top wall defining a fixing edge (21) facing away from the top wall of the lid and connected to the outer peripheral edge (13, 13') of the filter (4, 4') via an adhesive bond (22) in order to remove the filter (4) from the filtration device (1) by telescoping the lid (16) over the filter support (5), the annular inner wall (23) of the lid (16) projecting the top wall thereof a sufficient distance such that areas of a surface of the filter inward of the annular inner wall (23) contact the nutrient medium when the lid (16) is telescoped over the lower part (15, 15').

14. The nutrient medium unit of claim 13, wherein the inside diameter of the outer wall of the lid (16) is only slightly greater than the outside diameter of the filter support.

15. The nutrient medium unit of claim 1, wherein the adhesive bond (22) between the fixing edge (21) and filter (4) is interrupted in places in order to ensure an exchange of air.

16. The nutrient medium unit of claim 15, wherein the fixing edge (21) of the lid (16) is interrupted by at least one cutout in order to ensure an exchange of air.

17. The nutrient medium unit of claim 16, wherein the fixing edge (21) of the lid (16) is reduced to at least two fixing pins (29) via which the filter (4) can be connected to the lid (16).

18. The nutrient medium unit of claim 1, wherein the lid (16) has a recloseable gas-feed aperture in order to ensure an exchange of air.

19. The nutrient medium unit of claim 18, wherein the nutrient medium (17, 17') is formed from agar.

20. The nutrient medium unit of claim 19, characterized in that the filter (4) is designed as a membrane filter.

21. The nutrient medium unit of claim 1 wherein a lower part (3) of the device having a membrane filter comprises an attachment (2) or funnel (7) positioned over a base (6) or guides of the lower part (3) of the device such that an active filtration surface of the membrane filter Is positionable over the base (6) or the guides with an annular inner wall (23) of the lid (16) in a secure fashion outside the active filtration surface.

22. The nutrient medium unit of claim 21 wherein the lower part (3) is a disposable article and is made of plastic.

23. The nutrient medium unit of claim 21 wherein the filtration device (1) forms a disposable system with the lower part (3), the filter (4) and an attachment (2), and is made of plastic.

* * * * *